United States Patent [19]

Fritze et al.

[11] 4,219,398
[45] Aug. 26, 1980

[54] APPARATUS FOR CONTINUOUS MEASUREMENT OF GAS TRACES WITH ION-SENSITIVE ELECTRODES

[75] Inventors: Ulrich Fritze, Cologne; Heinz Herschinger, Leverkusen, both of Fed. Rep. of Germany

[73] Assignee: Bayer Aktiengesellschaft, Leverkusen, Fed. Rep. of Germany

[21] Appl. No.: 904,344

[22] Filed: May 9, 1978

[30] Foreign Application Priority Data

May 24, 1977 [DE] Fed. Rep. of Germany ....... 2723310

[51] Int. Cl.² ............................................. G01N 27/46
[52] U.S. Cl. .............................. 204/195 M; 204/1 T; 23/232 E; 422/98
[58] Field of Search .................... 23/232 E, 232 R; 422/98; 204/195 P, 195 M, 195 F, 195 R, 1 T

[56] References Cited

U.S. PATENT DOCUMENTS

| | | | |
|---|---|---|---|
| 2,760,922 | 8/1956 | Williams, Jr. | 422/98 X |
| 2,805,191 | 9/1957 | Hersch | 23/232 E X |
| 3,287,631 | 11/1966 | Stout, Jr. | 422/98 X |
| 3,540,851 | 11/1970 | Vree et al. | 23/232 E |
| 3,719,575 | 3/1973 | Niedrach et al. | 204/195 P |
| 3,915,646 | 10/1975 | Harris et al. | 23/232 E |
| 3,972,792 | 8/1976 | Laxen | 204/1 T X |
| 4,057,478 | 11/1977 | Bruckenstein et al. | 204/195 P |

Primary Examiner—Arthur C. Prescott
Attorney, Agent, or Firm—Sprung, Felfe, Horn, Lynch & Kramer

[57] ABSTRACT

The method is based on the gas which is to be examined being absorbed in a flowing liquid and then dissociated. The ions formed are detected with an ion-sensitive electrode. In order to obtain a high solubility and thus a high sensitivity, the absorption liquid together with the gas is continuously atomized, the liquid phase is subsequently separated off and is fed, in a continuous flow, through a measuring chain having an ion-sensitive electrode.

10 Claims, 3 Drawing Figures

APPARATUS FOR CONTINUOUS MEASUREMENT OF GAS TRACES WITH ION-SENSITIVE ELECTRODES

The invention relates to a method of measuring gas traces in which the gas to be examined is absorbed by a flowing liquid and the ions formed in the liquid by the gas are measured with an ion-sensitive electrode. The invention also relates to an apparatus for carrying out this method. It consists fundamentally of an electrochemical measuring chain with an ion-sensitive electrode and a reference electrode which are both in contact with a liquid absorbing the gas to be examined.

In accident prevention, the problem of the prompt detection of gases which are hazardous to the health, for example in laboratories, chemical production plant or of monitoring the air in large cities, has not yet been satisfactorily solved. In this context, "prompt" means that traces of the hazardous gas, i.e. fractions of a milliliter per cubic meter of ambient air, may be detected and trigger an alarm within a few seconds of the appearance of the hazardous gas, for example at a place of work. Another requirement of such an apparatus for measuring traces of gas and for giving a warning is that the apparatus is again ready for measuring traces of gas sufficiently quickly, i.e. within a few minutes of the appearance of relatively high concentrations of gas, for example in the order of magnitude of liters per cubic meter (short regeneration period). A gas trace apparatus is required to function with as little servicing as possible, i.e. a checking or correcting operation is required and the necessary auxiliary solutions or electrodes should have to be renewed only after relatively long intervals of time, for example, three weeks or more.

A known method for the sensitive detection of specific foreign gases, for example, in ambient air, involves feeding the ambient air through a suitable solution and the foreign gas absorbed by the solution forms ions which are detected by an ion-sensitive electrode. In order to be able to record changing concentrations of foreign gas—this being a basic requirement for an automatic instrument for measuring traces of gas—the absorption solution has to be continually renewed. For this purpose, the ambient air to be tested is fed in a continuous flow through the absorption solution. At a predetermined concentration of a foreign gas to be detected, the ratio of the ambient air stream ($m^3/h$) to the absorption solution stream ($m^3/h$) determines the concentration of the foreign gas absorbed in the solution. This concentration should lie within the linear region of the electrode characteristic curve; the electrode characteristic curve being a plot of the electrode potential (or measuring chain voltage) as a function of the ion concentration. Since all ion-sensitive electrodes only show a characteristic curve obtainable by measuring techniques above an electrode-specific minimum ion concentration, the ion concentration in the absorption solution should be above this threshold concentration.

A considerable disadvantage of the above described method results from the incomplete dissolution of the portion of the foreign gas to be detected in the absorption solution. This has a decisive effect on the sensitivity of the arrangement for measuring gas traces. In order to obtain the minimum ion concentration in the absorption solution, by these measuring techniques, the ambient air has to flow through a predetermined quantity of absorption solution (which is to be renewed after thirty seconds) for a predetermined period, for example thirty seconds. The promptness of measurement which can be achieved is limited by this provision. In addition, this requires a high consumption of absorption solution. In order to reduce the consumption of absorption solution, one might consider keeping the ratio of continuously flowing absorption solution stream ($m^3/h$) to ambient air stream ($m^3/h$) extremely low, for example $\leq 1:100$. This would however give rise to problems with flow and absorption which have not yet been solved in conventional apparatus.

An object of the invention is therefore to develop a method for measuring gas traces based on ion-sensitive electrodes to achieve a rapid response and a high sensitivity requiring a low consumption of absorption solution. These requirements are normally contradictory and could not be met simultaneously hitherto.

In accordance with the invention there is provided a method of measuring gas traces in which a gas to be examined is caused to be absorbed by a flowing absorption liquid by the continual atomization of the said absorption liquid together with the said gas, and the liquid phase is then separated off and fed in a continuous flow, through a measuring chain having an ion-sensitive electrode, which measuring chain measures the ions formed by the gas in the liquid.

The absorption liquid is preferably allowed to flow out via the free horizontal sensor disc of the ion-sensitive electrode under the force of gravity, and the flow is regulated so that a liquid column about 1 to 2 mm high is always maintained on the sensor disc and simultaneously makes contact with a reference electrode.

The flow-rates for the gas ($Q_G$) and the absorption liquid ($Q_F$) are advantageously regulated so that at least $Q_G = 2000\ Q_F$.

The invention also provides an apparatus for measuring gas traces comprising an atomizer having means for the introduction of a gas and an absorption liquid, a separating chamber connected to the atomizer, which separating chamber is connected via a liquid conductor to an electrochemical measuring chain arranged below the atomizer, the said electrochemical measuring chain having an ion-sensitive electrode an a reference electrode, said ion-sensitive electrode being provided with a sensor disc and said reference electrode being provided with a diaphragm, the said sensor disc being arranged horizontally so that an absorption liquid column wetting the entire surface and in contact with the said diaphragm is formed.

In an improved design, the atomizer nozzle, the separating chamber, and the measuring chain are installed in a protective container with feed pipes for the gas and the absorption liquid, and the gas suction pump is arranged in the outlet, at the bottom of the protective container.

The gas is separated from the absorption liquid in this separating chamber which is advantageously designed as a pipe widening in the direction of flow of the liquid, cut off obliquely at the lower end. In this manner, the solution which has precipitated on the wall, flows downwards and collects on the deepest point of the oblique cut. The solution which is being discharged is then fed via a hydrophilic liquid conductor, preferably a thin glass rod, to the free upward-pointing surface of a disc-shaped ion-sensitive sensor contained by an electrically non-conductive shaft in such a way that a liquid column from 1 to 2 mm high which completely covers the surface of the disc is formed between the end of the liquid conductor and the sensor disc under the influence of the surface forces. Complete coverage is important to ensure uninterrupted functioning of the sensor. If the sensor has a hydrophobic surface, then a completely wetting liquid column may be formed by covering the sensor disc with a thin hydrophilic and porous surface layer of alternatively covering it with a hydrophilic film which is capable of swelling.

The reference electrode pertaining to the measuring chain is arranged in such a way that it may also be wetted by the above-mentioned liquid column. This is advantageously achieved by the end of the reference electrode provided with a diaphragm being located just above the sensor disc and the above-mentioned liquid conductor being in contact with the lower end of the electrode shaft.

An advantage obtained with the invention is that a very high proportion of gas is absorbed, since the gas is mixed thoroughly with the absorption liquid when they are atomized. A high sensitivity is obtained in this way. Another substantial advantage is the extremely low consumption of absorption liquid which is derived from the special design of the measuring system. In contrast to the conventional apparatus, the measuring system requires only a very small volume of liquid which is continuously renewed. The small volume of liquid ensures rapid exchange of the liquid in the measuring system even with small liquid streams of the order of magnitude of 20 ml/h, so as to guarantee a rapid regeneration period ($\leqq 30$ seconds). The low liquid consumption allows substantially longer service lives in reltion to the former apparatus. Thus, for example, with the continuous operation, new absorption solution has to be poured into the storage container only every 3 to 4 weeks. The measuring system itself requires practically no servicing. The entire arrangement may be constructed compactly and placed easily in, for example, a housing of about 200 ml, because of its compact structure to small volume.

With reference to the accompanying drawings

Figure 1:
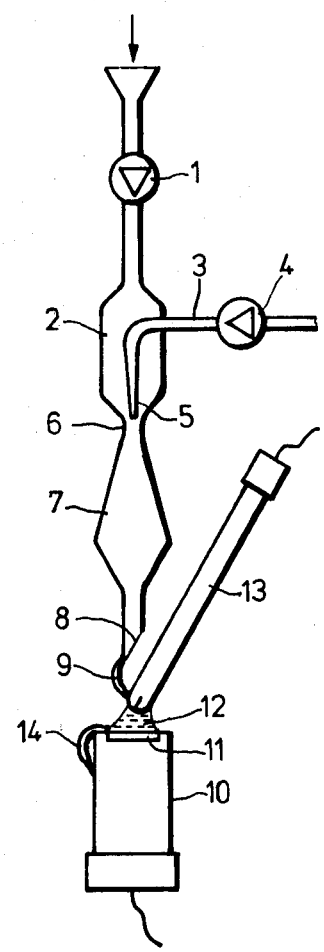
FIG. 1 shows the measuring arrangement.

In the measuring arrangement according to FIG. 1, the gas mixture $Q_G$ to be examined, for example ambient air, is sucked at a flow rate of, for example, 300 l/h by a suction pump (1) and flows into an atomizer (2). An absorption solution is introduced via a lateral connection (3) on the atomizer (2) by means of a metering pump (4) at, for example, 10 ml/h. The absorption solution stream $Q_F$ flows out through an atomizer nozzle (5), with for example $\phi = 0.6$ mm and is sprayed through the gas passing through concentrically in a narrow pipe (6), with for example $\phi = 3.5$ mm. The pneumatic atomizer causes intensive mixing of the gas with absorption liquid so that optimum conditions for high absorption may be achieved. The pipe shaped atomizer (2) widens at the lower end into a separating chamber (7). The liquid collects on the internal wall thereof and flows downwards as a thin film. In this way, the gas-liquid mixture present in the spraying area (6) is again broken down into a liquid and gaseous phase. The gas stream accelerates the delivery. The lower end (8) of the separating chamber (7) contracts and is cut off in an oblique cut and is fed via a hydrophilic liquid conductor (9). For example, a thin glass rod ($\phi = 1$ mm), to the free upward-pointing surface of a disc-shaped ion-sensitive sensor (11) contained by an electrically non-conductive shaft 10 in such a way that a liquid column (12), from 1 to 2 mm high, which completely covers the surface of the disc, is formed between the end of the liquid conductor (9) and the sensor disc (11) under the influence of forces of surface tension. Complete coverage is important for the uninterrupted electro-chemical functioning of the sensor. If a hydrophobic sensor material is provided, then the sensor disc is covered with a thin hydrophilic and porous gauze, for example glass fibre gauze or a film composed of a material which is capable of swelling, for example cellulose acetate film. In this way, it is possible to obtain a uniformly wetting liquid column (12) even with a hydrophobic sensor material. The liquid column (12) is also in contact with a reference electrode (13). Its lower end in contact with the liquid is provided with a diaphragm (13a). In the design shown here, the liquid conductor (9) ends at the end of the shaft of the reference electrode (13) on its outside. The diaphragm (13a) produces an electrical connection between the electrolyte in the reference electrode and the outside and thus with the liquid column (12). It is composed, in known manner, of a short rod of porous material, for example sintered ceramic material. The lower end of the reference electrode (13) is located about 1 to 2 mm above the surface of the sensor. The intermediate space is filled with the liquid column (12) which wets the diaphragm and the surface of the sensor. The liquid is removed from the surface of the sensor by another liquid conductor (14) in the form of a small bent glass rod which leads from the edge of the sensor to the sensor shaft. The absorption liquid then flows downwards evenly on the outside of the sensor shaft. This liquid control ensures that the liquid column (12) remains stationary in its geometry. If the absorption solution were dripped in or out irregularly, the liquid column would pulsate, thus producing interference in the measurements.

The majority of the measuring arrangement, in particular the atomizer arrangement (2), (3), (6), the separaring chamber (7) and the liquid conductor (8) and (14) are composed of glass. In theory, any other hydrophilic material may be used in its stead. The entire arrangement is constructed vertically so that the liquid flows from the top to the bottom over the horizontal ion-sensitive electrode. Slight deviations from the vertical position are, however, not critical. The measuring chain consisting of reference electrode (13) and ion-sensitive electrode (11) is a commercial component and need not therefore be described in more detail at this point. The potential difference obtained is measured in a conventional manner with a power-less measuring instrument at the terminals of the reference electrode (13) and the ion-sensitive electrode (11). A polarographic mode of operation may be used instead of measurement of potential, in which case, a suitable bias must be provided.

Figure 2:
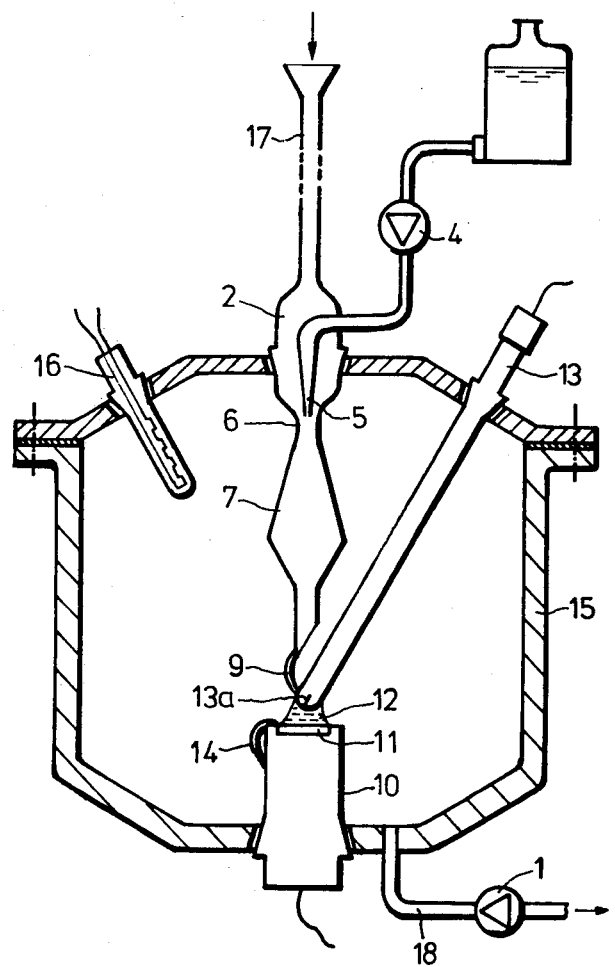
FIG. 2 shows a further embodiment of the measuring arrangement.

In the further embodiment in FIG. 2, the atomizer (2) and the measuring chain (11), (13) are installed in a protective housing (15). Suitable openings are provided in the protective housing (15) for the reference electrode (13), the shaft (10) with the ion-sensitive electrode (11) and for a temperature detector (16) for compensating for the temperature-dependence of the sensor in operation. The ambient air is drawn here via a sniffing pipe (17). The gas pump is not located upstream of the atomizer 2 as in FIG. 1, but at a lower outlet 18 of the protective container (15), that is to say the gas is sucked through the atomizer (2) and the separating chamber (7). In this way, gas is prevented from being lost in the gas delivery pump and the continuous discharge of absorption solution from the protective container (15) is ensured by the reduced pressure in the suction pipe 18 of the suction pump (1).

With the invention, a high degree of absorption and thus a marked increase in the concentration of the gas to be measured in the measuring solution (1:20,000) is obtained by atomization. As a consequence of this there is a correspondingly increased accuracy in detection. The high absorption of gas and the small volume of liquid in the measuring chain allow a drastic reduction in the consumption of absorption solution (about 250 ml/day). A rapid display of the measured value (90% of the time about 10 to 15 seconds) and a short regeneration time (about 5 minutes) are obtained at the same time. These properties are illustrated in more detail below in example of measurement.

Ambient air containing 5 ppm HCl was examined with the arrangement in FIG. 2. A 1/100 n potassium nitrate solution was used as absorption solution. The ion-sensitive electrode consisted of a silver-silver chloride electrode which responded essentially only to $Cl^-$ ions. The silver chloride was applied to a silver substrate as a thin layer. Such chloride electrodes are obtained, for example, from the company Colora-Meβ-technik.

Figure 3:
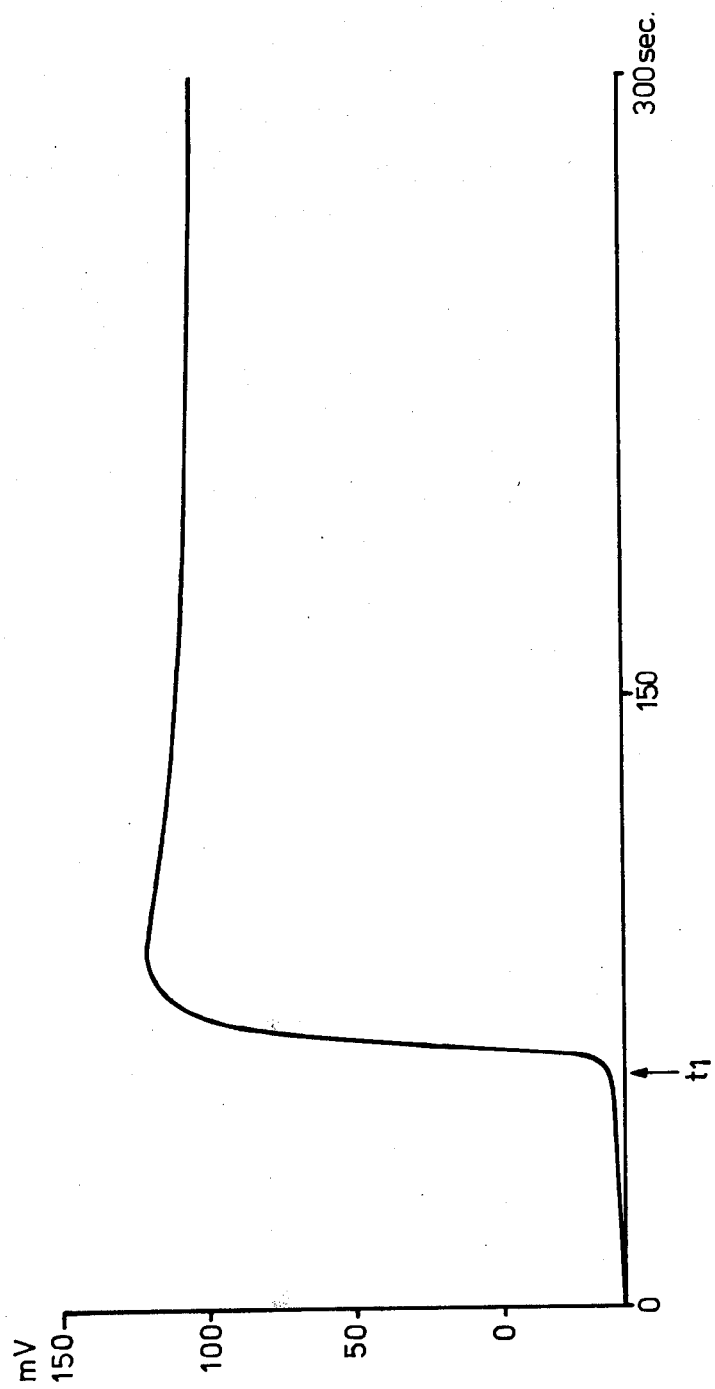
FIG. 3 shows a typical response curve for the measuring arrangement.

A gas stream of 1.3 m³/h of ambient air was drawn in using the suction pump (1). 20 ml/h of potassium nitrate solution from the supply container was simultaneously introduced into the arrangement by the metering pump (4). The path of the measuring signal in time is plotted in FIG. 3 (response curve). The potential difference measured on the reference electrode and on the Ag-AgCl-electrode is portrayed as the ordinate in millivolts. This potential represents a direct gauge for the chloride ion concentration up to the proportionality factor. The abscissa is calibrated in seconds. Initially only pure ambient air without HCl vapour is drawn in. 6.5 mm³/h of HCl gas is added at time $t_1$ to the ambient air stream with the aid of a metering device (not shown here). As a result, the measuring signal rises within about 20 seconds to the final value (−100 millivolts). The 90% value is obtained in 15 seconds. Initially of course, the 100% value is slightly exceeded but after a short time stationary final value is obtained.

A similar curve was produced when measuring hydrogen fluoride. In this case, a sensor disc composed of lanthanum chloride was used as the ion-sensitive electrode. The method according to the invention and the associated measuring arrangements fundamentally suitable for all gas components which form ions in a suitably selected absorption solution, which ions, in turn, may be detected by ion-sensitive electrodes, particularly by solid sensors.

What we claim is:

1. An apparatus for measuring gas traces comprising: atomizer means receptive of a gas to be examined and an absorption liquid to continuously atomize the two together; collecting means having an inlet receptive of the atomized gas and liquid and an outlet disposed below the inlet and for collecting the liquid phase saturated with the gas at a lower portion thereof adjacent the outlet; electrochemical cell means receptive of liquid for producing an electrical signal dependent in value on the number of ions formed by the gas therein comprising a horizontal disc sensor electrode and a reference electrode disposed above the sensor electrode; and means for continuously feeding all of the collected liquid phase through the electrochemical cell means during measurement of the ions to maintain a vertical column of liquid on the sensor electrode and in contact with the reference electrode.

2. The apparatus according to claim 1, wherein the sensor electrode comprises an ion selective electrode and the reference electrode comprises a diaphragm and wherein the means for continuously feeding comprises means for maintaining a liquid column on the disc to wet the entire surface thereof while simultaneously contacting the diaphragm.

3. The apparatus according to claim 1 or 2, wherein the feeding means maintains a liquid column from about 1 to 2 mm high on the sensor electrode.

4. The apparatus according to claim 1, wherein the collecting means comprises a chamber in communication with the inlet and outlet and wherein the inlet is disposed vertically above the outlet and the chamber is cylindrically symmetrical with respect to the vertical axis.

5. The apparatus according to claim 1 or 4, wherein the atomizer means and the collecting means are configured to maintain a unidirectional flow of the gas and liquid and subsequently the collected liquid phase from the receipt of the gas and liquid of the atomizer means, through the collector means of the collected liquid phase into the feeding means.

6. An apparatus according to claim 1, wherein the atomizer means, the collecting means and the electrochemical cell means are installed in a protective container with feed pipes for the gas and the absorption liquid and a gas suction pump is arranged in an outlet pipe at the bottom of the protective container.

7. An apparatus according to claim 1 or 6 wherein the collecting means comprises a pipe widening in the direction of flow of the liquid from the atomizer means to the electrochemical cell means and which is cut off obliquely at its lower end.

8. An apparatus according to claim 7 wherein the pipe consists of a glass rod.

9. An apparatus according to claims 1 or 2 wherein the surface of the sensor electrode is covered with one of a thin highly porous surface layer or a hydrophilic surface layer which is capable of swelling.

10. An apparatus according to claim 7 wherein the reference electrode comprises a tube provided with a diaphragm at its lower end arranged just above the sensor disc and said pipe is in contact with the reference electrode just above the diaphragm.

* * * * *

UNITED STATES PATENT AND TRADEMARK OFFICE
CERTIFICATE OF CORRECTION

PATENT NO. : 4,219,398
DATED : August 26, 1980
INVENTOR(S) : Ulrich Fritze et al It is certified that error appears in the above—identified patent and that said Letters Patent are hereby corrected as shown below:

Col. 3, line 31, "reltion" should be --relation--.

Col. 6, line 36, insert --and-- before "of".

Signed and Sealed this

Tenth Day of February 1981

[SEAL]

Attest:

RENE D. TEGTMEYER

Attesting Officer

Acting Commissioner of Patents and Trademarks